(12) United States Patent
Wang et al.

(10) Patent No.: US 10,137,464 B2
(45) Date of Patent: Nov. 27, 2018

(54) MULTI-FUEL-CANISTER INSECT REPELLENT SYSTEM

(71) Applicant: Thermacell Repellents, Inc., Bedford, MA (US)

(72) Inventors: Wender Wang, Bedford, MA (US); Steffen Koury, Bedford, MA (US); Brendan Crawford, Bedford, MA (US); Benjamin Hines, Bedford, MA (US); Tom Paganetti, Bedford, MA (US)

(73) Assignee: Thermacell Repellents, Inc., Bedford, MA (US)

( * ) Notice: Subject to any disclaimer, the term of this patent is extended or adjusted under 35 U.S.C. 154(b) by 0 days.

(21) Appl. No.: 15/794,448

(22) Filed: Oct. 26, 2017

(65) Prior Publication Data

US 2018/0117610 A1   May 3, 2018

Related U.S. Application Data (60) Provisional application No. 62/413,842, filed on Oct. 27, 2016, provisional application No. 62/417,008, filed on Nov. 3, 2016.

(51) Int. Cl.
*B05B 7/20* (2006.01)
*A01M 29/12* (2011.01)
(Continued)

(52) U.S. Cl.
CPC ............ *B05B 7/208* (2013.01); *A01M 1/2088* (2013.01); *A01M 29/12* (2013.01); *A61L 9/03* (2013.01);
(Continued)

(58) Field of Classification Search
CPC .......... B05B 7/208; F23D 14/28; F23C 13/02; A61L 9/03; A01M 1/2088; A01M 29/12; F23Q 3/002
See application file for complete search history.

(56) References Cited

U.S. PATENT DOCUMENTS 4,699,123 A * 10/1987 Zaborowski ............ F23D 14/28
126/409
5,476,376 A * 12/1995 Santhouse ............... F23D 14/18
126/406

(Continued)

FOREIGN PATENT DOCUMENTS

CA   2776282   11/2010
GB   2213379   8/1989

*Primary Examiner* — Regina M Yoo
(74) *Attorney, Agent, or Firm* — Levisohn Berger LLP (57) ABSTRACT

The invention provides a hydrocarbon-fueled device for heating and dispensing a volatile substance, such as an insect repellent. The device provides a long-lasting 48-hour fuel system, multiple fuel canisters that can be exchanged without interrupting the operation of the device, an illuminated indicator that provides a visible indication of the operating state of the device from any viewing angle, and a flame-extinguishing safety lid. During the warm-up phase, the indicator indicates this state by pulsing. Once the device reaches operating temperature, the indicator emits a steady light, indicating proper operation. In the event that the device cools below the operating temperature, the light will pulse, alerting the user to check the flame and/or fuel supply. The user can initiate complete, properly-controlled operation of all functions of the device via the operation of a single on-off switch.

24 Claims, 6 Drawing Sheets

(51) Int. Cl.
   *F23Q 3/00*      (2006.01)
   *A01M 1/20*      (2006.01)
   *A61L 9/03*      (2006.01)
   *F23C 13/02*     (2006.01)
   *F23D 14/28*     (2006.01)

(52) U.S. Cl.
   CPC .............. *F23C 13/02* (2013.01); *F23D 14/28* (2013.01); *F23Q 3/002* (2013.01); *F23N 2031/22* (2013.01); *F23N 2041/10* (2013.01)

(56) References Cited

U.S. PATENT DOCUMENTS

| | | | |
|---|---|---|---|
| 5,700,430 A | | 12/1997 | Sonnema |
| 5,928,605 A | * | 7/1999 | Bonnema ............ A01M 1/2088 126/401 |
| 6,244,853 B1 | | 6/2001 | Oglesby et al. |
| 2016/0286927 A1 | | 10/2016 | Winkler et al. |

* cited by examiner

MULTI-FUEL-CANISTER INSECT REPELLENT SYSTEM

REFERENCE TO PRIOR APPLICATIONS

This application claims priority of U.S. Provisional application No. 62/413,842, filed Oct. 27, 2016, and U.S. Provisional application No. 62/417,008, filed Nov. 3, 2016, the contents of both of which are incorporated herein by reference.

FIELD OF THE INVENTION

This invention relates to hydrocarbon-fueled insect repellent devices.

BACKGROUND OF THE INVENTION

The prior art discloses devices which utilize a fuel canister to supply fuel to burners which heat and vaporize an insect repellent composition. The canisters generally contain propane and/or butane under sufficient pressure to liquefy the gases. In order to compensate for variations in vapor pressure, which varies with fuel composition and temperature, these prior art devices use pressure regulators to help control gas flow. Representative devices are described in U.S. Pat. Nos. 4,733,651; 4,759,343; 4,699,123; and 5,700,430; and U.S. patent application Ser. No. 14/848,052 (filed Sep. 8, 2015) and U.S. Provisional Patent Application (filed Feb. 23, 2016) 62/298,539. The contents of these prior patents and applications are incorporated herein by reference in their entireties.

During operation of these prior art devices, when a cartridge containing the gas fuel is inserted into the appliance, the cartridge valve is not opened and fuel does not flow to the pressure regulator. When the appliance is turned on, the regulator pushes a plunger into the cartridge valve, opening it and allowing gas to flow. When a predetermined pressure is reached, the gas acts upon the diaphragm in the regulator to reduce or stop the gas flow by closing the cartridge valve. Thus, while the part of the regulator that senses pressure is in the appliance, the device that controls gas flow is in the valve built into the cartridge. Such a system limits the device to the use of a single attached cartridge.

There are numerous camping stoves in the prior art, for cooking and for heating, which rely on gas supplied by canisters but which do not have a pressure regulator. The gas flow in these devices is user-controlled via needle valves. Some stove models do have regulators, but they still have needle valves for user control of the gas flow.

The combustion devices described above generally must be visually inspected to determine their operating status. If the flame is contained internally, this may involve peering into a view hole to see if a flame or glowing indicator is visible. If there is no visible flame or indicator, it is rarely clear whether gas is flowing into the device. The user is usually reduced to listening closely for the sound of flowing gas, which can be a risky undertaking with a hot device.

Many campers, RV users and backpackers who enjoy the outdoors are subject to insect attacks. The prior devices covered by the above-listed patents are limited to the amount of fuel because of the size of the cartridge. Longer-term use of insect repellent devices powered by a portable fuel source is desirable, for example when users wish to have overnight protection. There remains a need for devices with operating times not limited by the fuel contained in a single canister, for devices which do not require the user to adjust a needle valve to reach and maintain a desired operating temperature, and for devices that clearly indicate their operating status to the user.

BRIEF DESCRIPTION

The present invention improves upon the teachings of the '430 patent, which is directed to a device for dispensing a volatile substance, such as an insect repellent, as well as the teachings of the valve regulation systems of the other listed patents.

The commonly available larger-capacity fuel canisters may contain propane or butane, and often contain a mixture of the two, under sufficient pressure to liquefy the gases. In order to compensate for variations in vapor pressure, which varies with fuel composition and fuel temperature, the present invention employs a pressure regulator to help finely control gas flow from such canisters.

The device of the invention is designed to accept multiple gas canisters, and automatically opens the canister valves when they are attached. Attachment of a canister also automatically opens a valve controlling admission of gas to the regulator. Removal of a canister closes both the canister valve and the internal valve, so as to permit the device to continue operating on fuel from one or more other attached canisters. This is an advantage over single-canister devices, which must be shut down when changing canisters.

An important aspect of the present invention is the ability to accurately control fuel flow to the heating element for the insect repellent device. The careful and effective control of fuel flow is an important safety aspect as well as a performance feature of such devices, because the user is generally unable to judge what constitutes an appropriate rate of combustion and rate of insect repellent release. The present invention provides the required precise control, while providing the user with the simplicity and convenience of on/off operation.

Standard fuel canisters come with their own internal valves, but these valves are designed for on/off operation, not for fine flow control. As there are no standards specifying precise dimensions for the valve components, consistent valve control from one brand of canister to another is problematic for an attached appliance. In particular, the degree of control and quality of construction of such valves is not adequate when trying to control gas flow to an insect repellent device. Such devices include a heating plate with an impregnated mat thereabove, wherein the heating plate causes the impregnated mat to volatilize and disperse insect repellent chemicals to provide a reasonably sized insect-free area. Proper function depends on heating the impregnated mat to within an appropriate temperature range, which in turn is highly dependent on the fuel flow rate.

The device of the present invention includes a compact, internal pressure regulator to regulate gas flow, and to thereby maintain and control temperature to heat the plate and heat the mat thereupon to dispense volatile substances impregnated into the mat. When fuel canisters are installed, spring-loaded pins in the device press against and open the valves in the canisters, and also open valves admitting gas to the high-pressure side of the regulator. The pressure regulator controls a regulator valve, which precisely meters the gas flowing to the burner, thereby controlling the temperature of the heating plate and the rate of vaporization of the volatile materials within the mat.

The device also features a flame-extinguishing lid, which operates in conjunction with an exhaust gas re-entry port to force oxygen-depleted exhaust gases into the air supply for the burner. This extinguishes the flame, and prevents the device from operating with the lid in place, thereby avoiding the damage and dangers associated with overheating.

BRIEF DESCRIPTION OF THE DRAWINGS

The invention is shown in greater detail in the illustrative drawings, of which.

DETAILED DESCRIPTION

Broadly, the invention provides a gas-fueled, portable device for dispensing a heat-volatilizable substance. The device comprises plurality of canister receiving cavities, each of which is configured to receive and reversibly engage with a fuel canister. Engagement of each canister with a canister receiving cavity opens an outlet valve in the canister, opens a receiving valve in the receiving cavity, and thereby admits gaseous fuel into a pressure regulator via a pressure regulator valve.

A valve switch, operably connected to the pressure regulator valve and operable by a user, has an off position and an on position, wherein movement of the valve switch by the user from the off position to the on position opens the pressure regulator valve.

An electrical switch is also activated by the valve switch, and is operably connected to a battery and a controller, wherein movement of the valve switch by the user from the off position to the on position closes the switch and energizes the controller.

The device further comprises a temperature sensor in thermal contact with a combustion chamber and operably connected to the controller, and a light source operably connected to the controller. The controller, when energized, energizes the light source and causes the light source to enter into either of two indicator states that are visually detectable by the user. If the temperature sensor detects that the combustion chamber is below a predetermined operating temperature, the controller cause the light source to enter into the first indicator state. If the temperature sensor detects that the combustion chamber is at or above the predetermined operating temperature, the controller cause the light source to enter into the second indicator state.

The pressure regulator is in fluid communication with the pressure regulator valve, so that the pressure regulator operates the pressure regulator valve so as to maintain a predetermined gas pressure downstream of the pressure regulator. A fuel combustion chamber is downstream of, and in fluid communication with, the pressure regulator. The combustion chamber may contain a flame burner nozzle or a catalytic burner. A sole plate is in thermal communication with the combustion chamber, and has a heated surface upon which the heat-volatilizable substance is placed.

A solid state temperature sensor is operably connected to a control circuit to measure temperature and illuminate (and optionally pulse) pulse one or more LEDs when a predetermined temperature is reached. The indicator light(s) are visible through a translucent lens. The LED may indicate that the gas is on (e.g. by blinking) and that the operating temperature has been reached (e.g. by emitting a steady light). Optionally, differently colored LEDs may be employed to indicate the two operational states.

The device of the invention features an independent regulator that does not use the cartridge valves to control the flow of gas during operation.

The attached drawings show a particular embodiment of the present invention.

Figure 1:
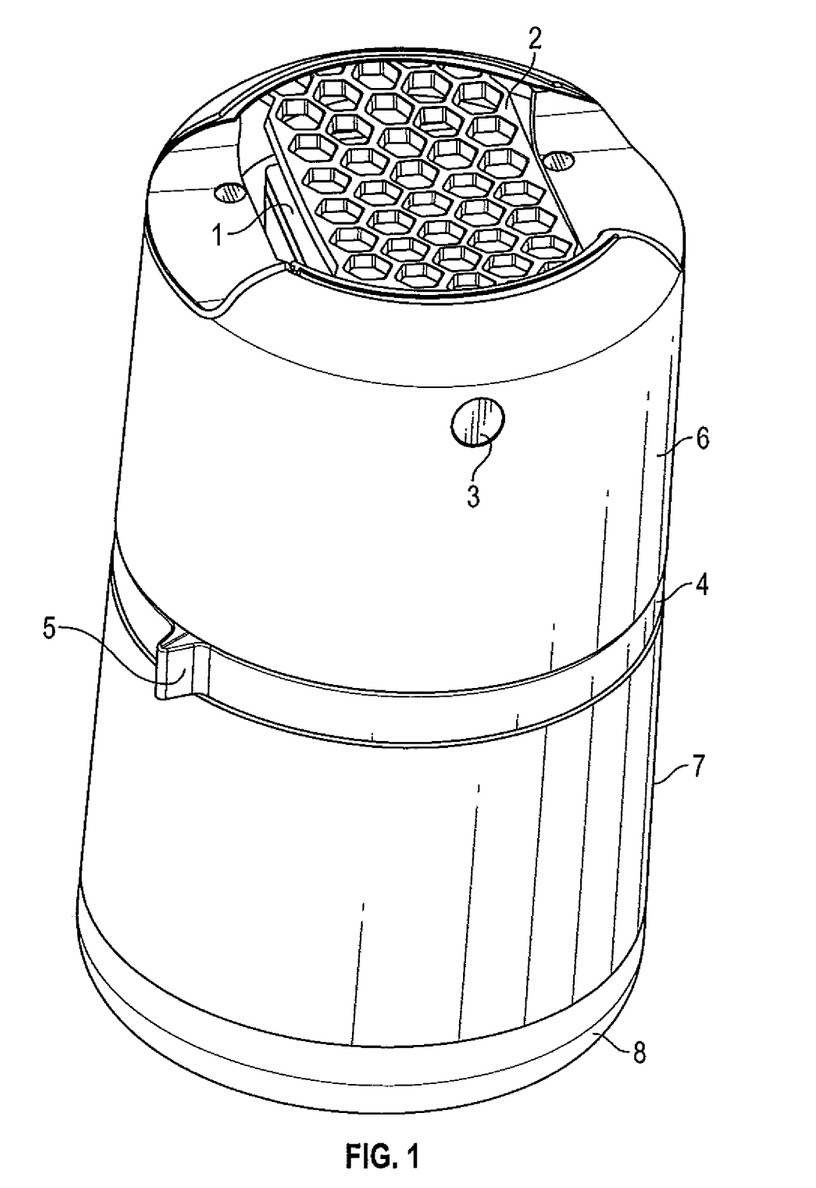
FIG. 1 is a perspective drawing showing an exterior view of a representative device according to the invention.

FIG. 1 shows an external perspective view of a representative embodiment of the invention. An insect repellent composition is dispersed within an absorbent mat 1, which rests underneath a protective grill 2. Grill 2 is formed with a concave shape, so that condensed insect repellant composition flows by gravity toward the center of the grill, collects, and eventually drips back onto mat 1. This feature prevents the horizontal capillary flow of condensed repellant, which in prior art devices often results in contamination of other surfaces of the device and renders the device messy and in need of frequent cleaning. The body of the illustrated device comprises upper shell 6, lower shell 7, and bottom cover 8. A transparent or translucent window 3 permits observation of the LED indicators described below. A circular band 4 is slidable around the body, and serves to open the regulator's gas flow control valve and, in the illustrated embodiment, when slid to its farthest position activates a piezoelectric igniter. A projecting tab 5 enables the user to slide the band by applying force with a finger, initiating gas flow, igniting the burner, and by moving the band to the closed position, cutting off gas flow and shutting down the device.

In certain embodiments, the combustion chamber may comprise a catalytic burner, in which case there is no need for a piezoelectric igniter.

Figure 2:
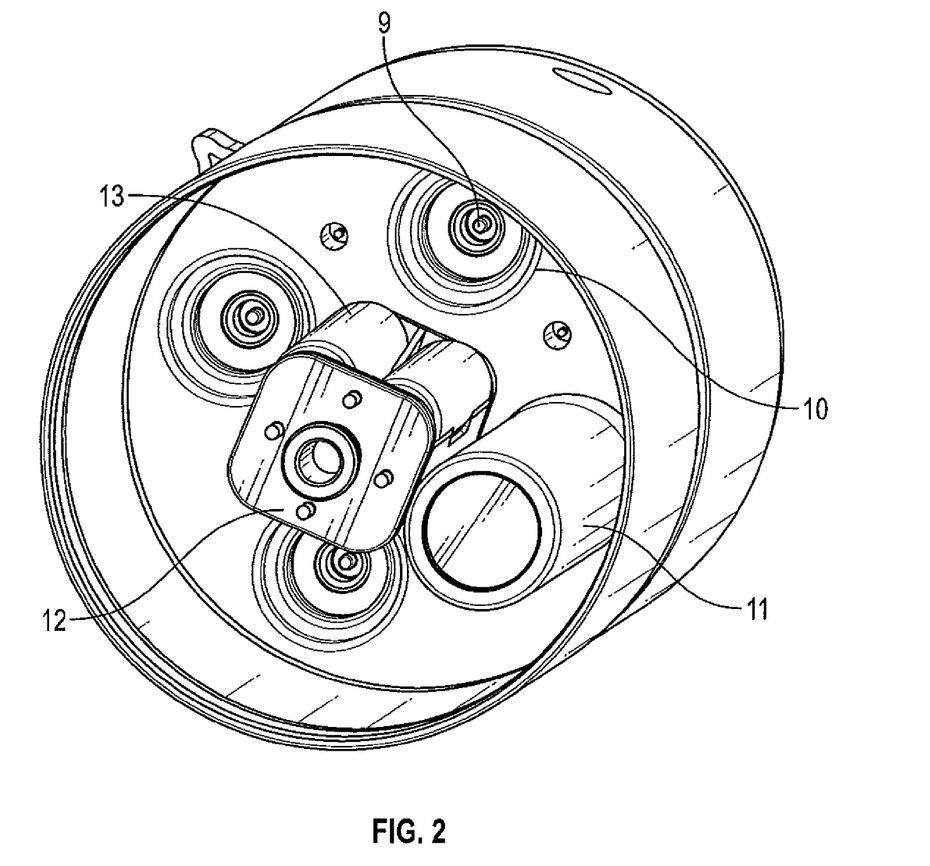
FIG. 2 is a bottom perspective view, with the bottom cover removed.

FIG. 2 shows a view from the bottom with the bottom cap removed. A check valve stem 9 is centered in the cartridge receiving cavity 10. A cartridge 11 is shown threaded into one of the cartridge attachment points. A battery holder 12 along with batteries 13 is located so as to be accessible for battery replacement. The batteries provide electrical current for the appliance status indicator.

Figure 3:
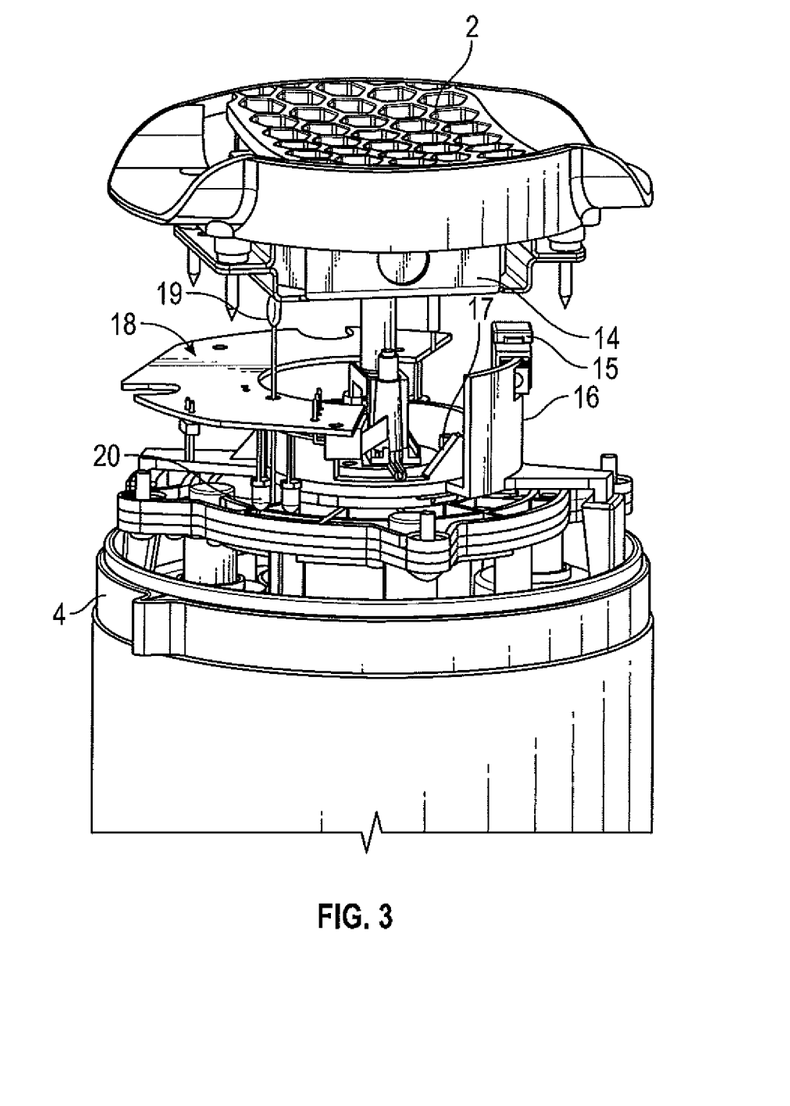
FIG. 3 is a view revealing both the gas control and the electrical components.

FIG. 3 shows a side view with the upper housing removed. The grill 2 is located above the combustion chamber 14. A piezoelectric igniter is positioned so that when circular band 4 is rotated to the full counter clockwise position, the on position, its cam surface 16 will actuate the igniter. Also, a second cam 17 attached to circular band 4 opens the regulator valve for fuel to flow. In the illustrated embodiment, as circular band 4 is rotated to the on position, it also closes an electrical circuit allowing current to flow to printed circuit board 18, which supports a simple controller. The controller then causes LED 20 to blink on and off until temperature sensor 19 detects that operating temperature has been reached. LED 20 will thereafter be held continuously on by the controller, until the appliance cools or the band 4 is returned to the off position. Should the fuel run out, or the flame be extinguished for any other reason, temperature sensor 19 will detect cooling below the operating temperature, and the controller will again cause the LED 20 to blink on and off.

Figure 4:
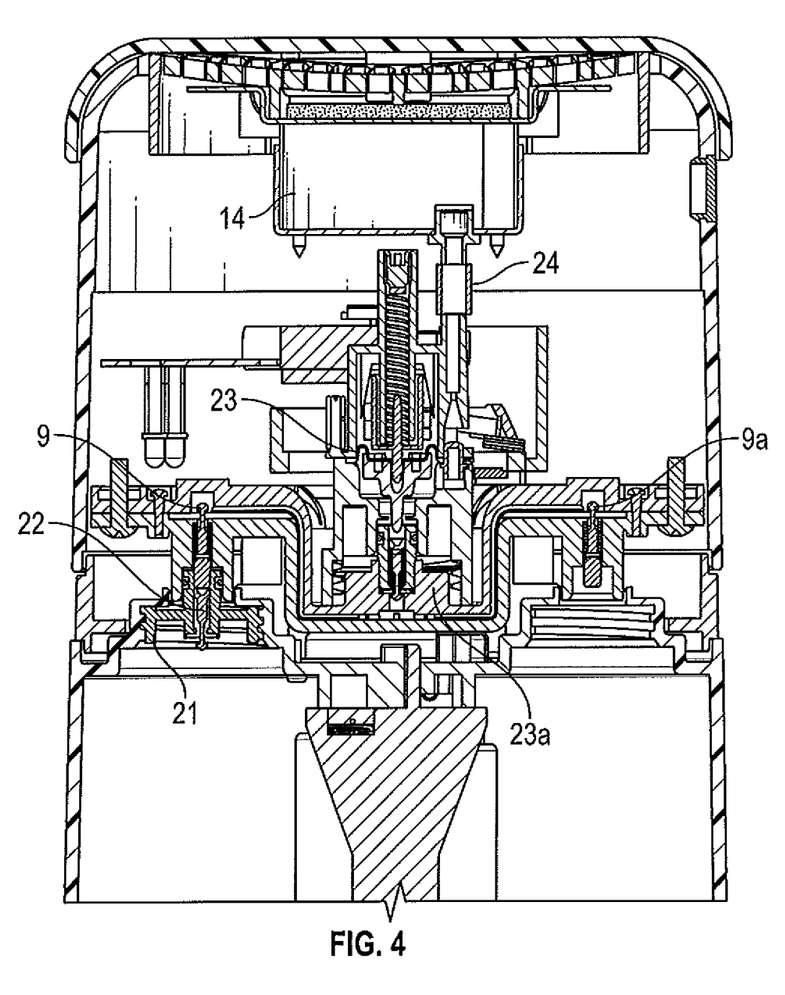
FIG. 4 is a cutaway/cross section of the elements shown in FIG. 3.

FIG. 4 illustrates a canister with canister valve threads 21 engaging complimentary threads in one of the canister receiving cavities. In the illustrated embodiment, the canister bears male threads 21, which mate with complimentary female threads in the receiving cavity. When the canister is installed, the spring-loaded plungers of both the canister outlet valve 22 and the receiving valve 9 are displaced into their open positions. Receiving valve 9a is shown in the closed state, which is the default position for the receiving valves when no canister is attached. The gas exits from each open receiving valve, passes to regulator valve 23a, and if valve 23a is open, the gas passes onward to the regulator 23. Gas is metered through valve 23a by the regulator, so as to be delivered at a pre-set pressure into the connecting tube 24, where it is mixed with air and then passes to a burner. Connecting tube 24 is integral to a heat box, which is otherwise omitted from FIG. 4 for clarity and is shown separately in FIG. 6.

Figure 5:
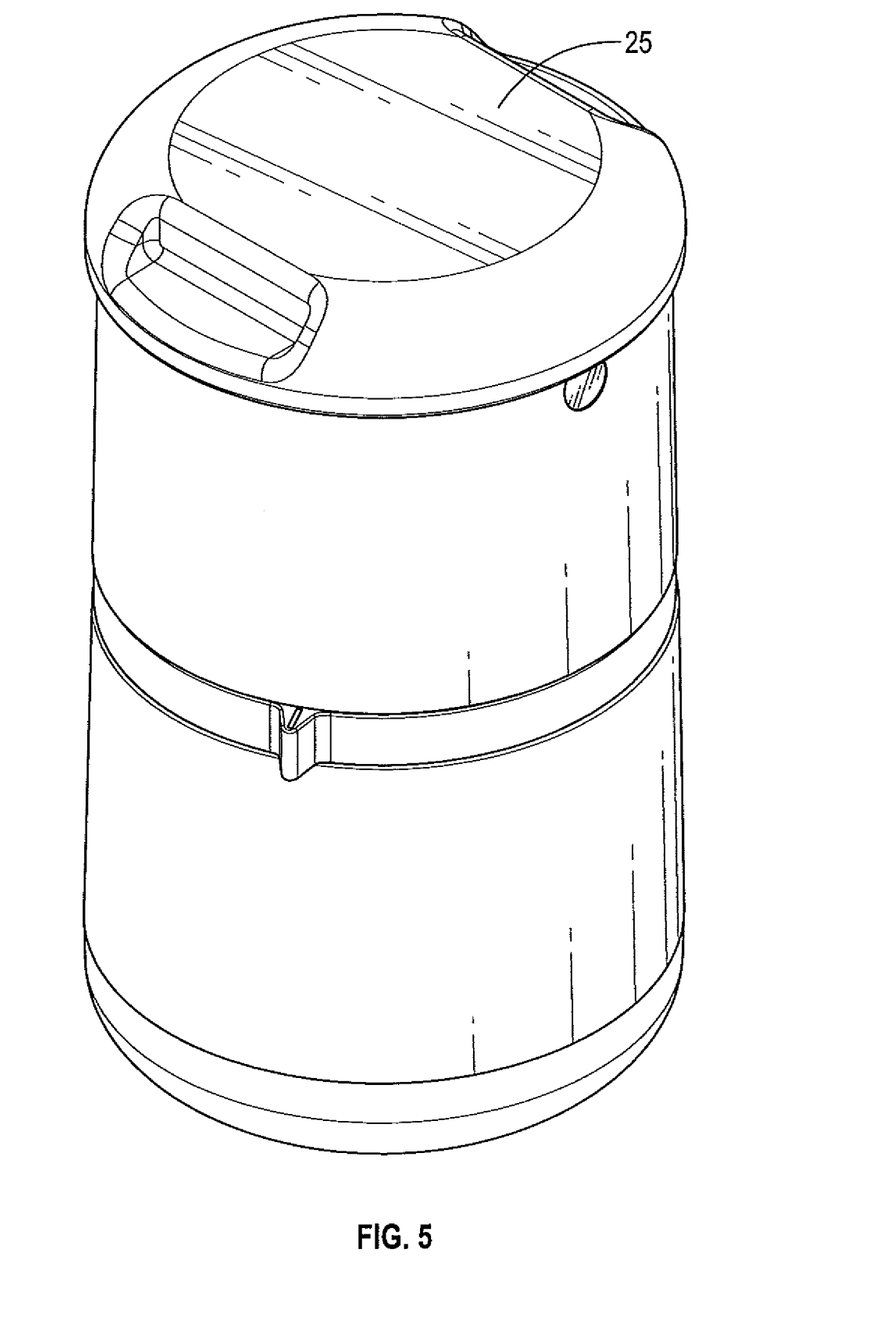
FIG. 5 is a perspective drawing showing an exterior view of the embodiment shown in FIG. 1, with a flame-extinguishing lid attached.

FIG. 5 illustrates the device with lid 25 attached. Attachment of the lid protects the internal components from dirt and weather, and also serves to extinguish the flame within the device if the user has neglected to do so. When the lid is pressed into place, it forces exhaust gases, which are depleted in oxygen and rich in carbon dioxide, through an exhaust re-entry port (see FIG. 6).

Figure 6:
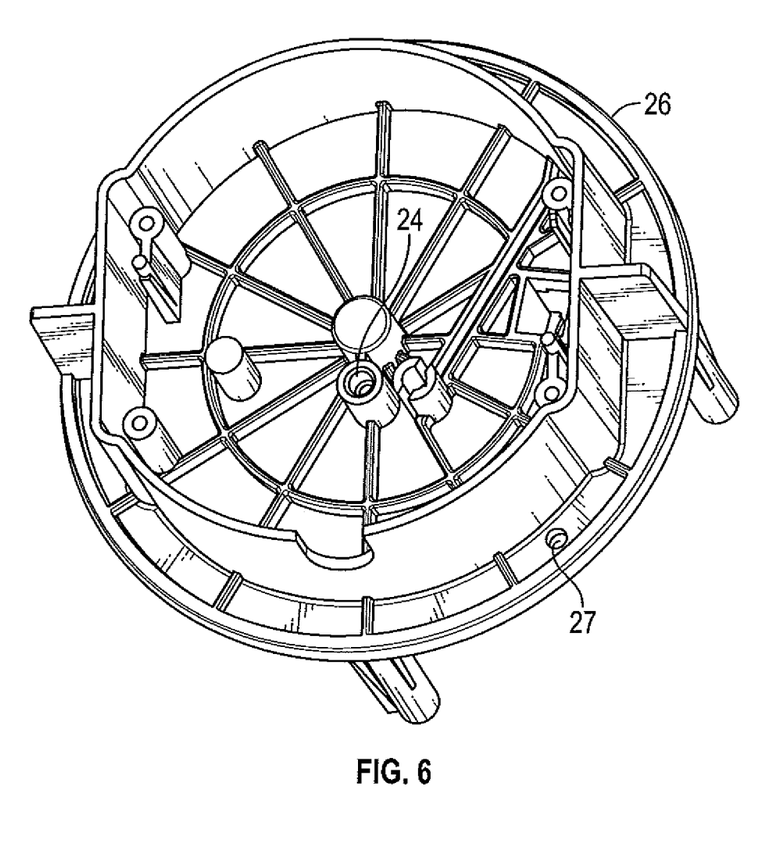
FIG. 6 is a perspective view of the interior of the heat box.

FIG. 6 illustrates the interior of the heat box 26, with connecting tube 24 and exhaust re-entry port 27 indicated. When the lid 25 is snapped into place, oxygen-depleted exhaust gas surrounding the combustion chamber 14 is displaced through the exhaust re-entry port 27 and into the air space below the heat box 26, where it combines with the fuel at connecting tube 24. The exhaust gas, being low in oxygen and rich in carbon dioxide, is not capable of supporting combustion, and the flame is thereby extinguished.

This invention combines a long-lasting 48-hour fuel system, the removal and replacement of gas canisters without interrupting operation, and a flame-extinguishing safety lid. The invention also provides an illuminated indicator that provides a visible indication of the operating state of the device, preferably in the form of an illuminated ring that can be seen from any viewing angle. During the warm-up phase, the light ring preferably pulses. Once the device is up to temperature, the ring preferably is illuminated with a steady, unobtrusive glow, indicating proper operation and the presence of an insect-free zone. In the event that fuel runs low, causing the device to cool below operating temperature, the light will revert to pulsing, alerting the user to check the fuel cartridges.

This invention is highly effective, safe, and simple to operate, utilizing up to four fuel cartridges and reducing the need to refuel during or between uses.

It should be understood that a single preferred embodiment has been described herein, to provide the best illustration of the principles of the invention and its practical application. The description and drawings are intended to enable one of ordinary skill in the art to make and use the invention in this and in other embodiments, with such modifications as may be desired or suited to the particular use contemplated.

The invention claimed is:

1. A gas-fueled, portable device for dispensing a heat-volatilizable substance, comprising:
   (a) a plurality of canister receiving cavities, each of which is configured to receive and reversibly engage with a fuel canister, wherein engagement of each fuel canister with the canister receiving cavity opens an outlet valve in the fuel canister, opens a receiving valve in the canister receiving cavity, and thereby admits gaseous fuel into a pressure regulator valve;
   (b) a valve switch operably connected to the pressure regulator valve and operable by a user, the valve switch having an off position and an on position, wherein movement of the valve switch by the user from the off position to the on position opens the pressure regulator valve, thereby permitting the gaseous fuel to flow into a pressure regulator in fluid communication with the pressure regulator valve;
   (c) wherein the pressure regulator operates the pressure regulator valve so as to maintain a predetermined gas pressure downstream of the pressure regulator valve;
   (d) a fuel combustion chamber downstream of and in fluid communication with the pressure regulator; and
   (e) a sole plate in thermal communication with the fuel combustion chamber and having a heated surface;
   wherein the pressure regulator valve meters the flow of the gaseous fuel to the fuel combustion chamber at a predetermined pressure, so as to sustain a predetermined rate of fuel combustion which heats the sole plate to a predetermined temperature sufficient to dispense the heat-volatilizable substance from the heated surface.

2. The gas-fueled, portable device according to claim 1, further comprising:
   (f) an electrical switch activated by the valve switch and operably connected to a battery and a controller, wherein movement of the valve switch by the user from the off position to the on position closes the electrical switch and energizes the controller;
   (g) a temperature sensor in thermal contact with either the fuel combustion chamber or the sole plate, and operably connected to the controller; and
   (h) a light source operably connected to the controller, the controller energizing the light source and causing the light source to enter into either
      (i) a first indicator state that is visually detectable by the user if the temperature sensor detects that the fuel combustion chamber is below a predetermined operating temperature, or
      (ii) a second indicator state that is visually detectable by the user if the temperature sensor detects that the fuel combustion chamber is at or above a predetermined operating temperature.

3. The gas-fueled, portable device according to claim 2, wherein the first indicator state is a flashing of the light source, and the second indicator state is a steady illumination of the light source.

4. The gas-fueled, portable device according to claim 3, wherein the first and second indicator states are visible to the user from all positions in a 360° range of viewing angles around the gas-fueled, portable device.

5. The gas-fueled, portable device according to claim 4, further comprising a piezoelectric fuel igniter.

6. The gas-fueled, portable device according to claim 5, wherein the piezoelectric fuel igniter is activated by movement of the valve switch by the user from the on position to an ignition position.

7. The gas-fueled, portable device according to claim 3, further comprising a piezoelectric fuel igniter.

8. The gas-fueled, portable device according to claim 7, wherein the piezoelectric fuel igniter is activated by movement of the valve switch by the user from the on position to an ignition position.

9. The gas-fueled, portable device according to claim 2, wherein the first indicator state is a first color of the light source, and the second indicator state is a second color of the light source.

10. The gas-fueled, portable device according to claim 9, wherein the first and second indicator states are visible to the user from all positions in a 360° range of viewing angles around the gas-fueled, portable device.

11. The gas-fueled, portable device according to claim 10, further comprising a piezoelectric fuel igniter.

12. The gas-fueled, portable device according to claim 11, wherein the piezoelectric fuel igniter is activated by movement of the valve switch by the user from the on position to an ignition position.

13. The gas-fueled, portable device according to claim 9, further comprising a piezoelectric fuel igniter.

14. The gas-fueled, portable device according to claim 13, wherein the piezoelectric fuel igniter is activated by movement of the valve switch by the user from the on position to an ignition position.

15. The gas-fueled, portable device according to claim 2, wherein the first and second indicator states are visible to the user from all positions in a 360° range of viewing angles around the gas-fueled, portable device.

16. The gas-fueled, portable device according to claim 15, further comprising a piezoelectric fuel igniter.

17. The gas-fueled, portable device according to claim 16, wherein the piezoelectric fuel igniter is activated by movement of the valve switch by the user from the on position to an ignition position.

18. The gas-fueled, portable device according to claim 2, further comprising a piezoelectric fuel igniter.

19. The gas-fueled, portable device according to claim 18, wherein the piezoelectric fuel igniter is activated by movement of the valve switch by the user from the on position to an ignition position.

20. The gas-fueled, portable device according to claim 2, wherein the fuel combustion chamber comprises a catalytic burner.

21. The gas-fueled, portable device according to claim 1, further comprising a piezoelectric fuel igniter.

22. The gas-fueled, portable device according to claim 21, wherein the piezoelectric fuel igniter is activated by movement of the valve switch by the user from the on position to an ignition position.

23. The gas-fueled, portable device according to claim 1, wherein the fuel combustion chamber comprises a catalytic burner.

24. The gas-fueled, portable device according to claim 1, wherein the gaseous fuel is mixed with air in a connecting tube, passed to a burner, and combusted within the combustion chamber, the combustion chamber being contained within a heat box, and the heat box having an exhaust re-entry port disposed so as to admit combustion exhaust gases to the connecting tube when the combustion exhaust gases within the heat box are displaced.

* * * * *